United States Patent
Ellenberger et al.

(10) Patent No.: US 6,613,792 B1
(45) Date of Patent: Sep. 2, 2003

(54) TREATMENT OF PREMENSTRUAL SYNDROME AND MENOPAUSE

(75) Inventors: Suzanne R. Ellenberger, Woodward, OK (US); William P. Ellenberger, Woodward, OK (US); G. Merrill Andrus, Orem, UT (US)

(73) Assignee: Designed Nutritional Products, Inc., Vineyard, UT (US)

( * ) Notice: Subject to any disclaimer, the term of this patent is extended or adjusted under 35 U.S.C. 154(b) by 0 days.

(21) Appl. No.: 09/365,425

(22) Filed: Aug. 2, 1999

(51) Int. Cl.$^7$ .................... A61K 31/405; A61K 31/40
(52) U.S. Cl. ............................ 514/415; 514/419
(58) Field of Search ........................... 514/415, 419

(56) References Cited

U.S. PATENT DOCUMENTS 5,895,787 A * 4/1999 Arffmann et al. ............ 514/415

FOREIGN PATENT DOCUMENTS

WO    WO 99/17768    4/1999

OTHER PUBLICATIONS

Derwent abstract (File: DWPI) Derwent Acc No. 1995–283604, abstract of WO 9520972 A1 (Grow, D. et al.), Aug. 1995.*
Notification of Transmittal of the International Search Report or the Declaration.
Jellinck et al., "Influence of indole–3–carbinol on the hepatic microsomal formation of catechol estrogens", Steroids, 1991, vol. 56, No. 8, pp. 446–450.
Bennett, Robert, "Fibromyalgia and the Disability Dilemma", Arthritis & Rheumatism, vol. 39, No. 10, pp. 1627–1634, Oct. 1996.
Carette, Simon, "Fibromyalgia 20 years later: What Have We Really Accomplished?", The Journal of Rheumatology, 22:4, pp. 590–594, 1995.
Designed Nutritional Products, "Product Information", 1 sheet, Mar. 1, 1997, I3C$^{TH}$, Catalog No. 2704.
Hadler, Nortin M., "If You Have to Prove You Are Ill, You Can't Get Well", Spine, vol. 21, No. 20, pp. 2397–2400, 1996.
Life Plus Foundation, "Relief From Chronic Fatigue Syndrome", Internet web site information, 7 pages, Jul. 9, 1997.
Michnovicz et al., "Changes in Levels of Urinary Estrogen Metabolites After Oral Indole–3–Carbinol Treatment in Humans", Journal of the National Cancer Institute, vol. 89, No. 10, pp. 718–723, May 21, 1997.
Michnovicz et al., "Dietary Cytochrome P–450 Modifiers in the Control of Estrogen Metabolism", Food Phytochemicals I: Fruits and Vegetables, pp. 282–293, 1994.
Nye, David A., "Fibromyalgia—a guide for patients", Sapient Health Network, 7 pages, Aug. 13, 1995.
Nye, David A., "Fibromyalgia—A Physician's Guide", Sapient Health Network, 9 pages, 1995.
Physical Medicine Research Foundation, "The Fibromyalgia Syndrome: A Consensus Report on Fibromyalgia and Disability", The Journal of Rheumatology, 23:3, pp. 534–539, 1996.
Romano et al., "Fibromyalgia 20 Years Later: What Have We Really Accomplished?", The Journal of Rheumatology, 23:1, pp. 192–194, 1996.
Thrive @ the healthy living experience, "Chronic Pain", 6 pages, 1996.
Wolfe et al., "Aspects of Fibromyalgia in the General Population: Sex, Pain Threshold, and Fibromyalgia Symptoms", The Journal of Rheumatology, 22:1, pp. 151–156, 1995.
Wolfe, Frederick, "Fibrositis, Fibromyalgia, and Musculoskeletal Disease: The Current Status of the Fibrositis Syndrome", Arch Phys Med Rehabil, vol. 69, pp. 527–531, Jul. 1988.
Wolfe et al., "The Prevalence and Characteristics of Fibromyalgia in the General Population", Arthritis & Rheumatism, vol. 38, No. 1, pp. 19–28, Jan. 1995.
Wolfe, Frederick, "When To Diagnose Fibromyalgia", Diagnostic Issues, vol. 20, No. 2, pp. 485–501, May 1994.

* cited by examiner

Primary Examiner—Russell Travers

(57) ABSTRACT

A method of treating premenstrual syndrome and menopausal symptoms in a patient, the method comprising: administering to the patient an 1H-indole-3-methanol compound (e.g., 1H-indole-3-methanol; ascorbigen) in a medically acceptable manner in a pharmaceutically effective amount. It has been found that the administration of such indoles, particularly, 1H-indole-3-methanol, greatly relieves the symptoms of PMS. Patients with PMS have reported decreased menstrual cramping, decreased menstrual flow, shorter duration of menses, decreased fatigue, less frequent headaches, improved mood, and decreased bloating resulting from the oral administration each day or during specific portions of the menstrual cycle of pharmaceutically effective amounts of dietary indoles derived from 1H-indole-3-methanol. It has also been found that the administration of such indoles, particularly, 1H-indole-3-methanol, greatly relieves the symptoms of menopause.

20 Claims, No Drawings

TREATMENT OF PREMENSTRUAL SYNDROME AND MENOPAUSE

TECHNICAL FIELD

This invention relates to the use of various naturally occurring compounds to treat the symptoms of diseases, and, more particularly, to the use of the natural product indole-3-methanol and related compounds to alleviate the symptoms associated with premenstrual syndrome and menopause.

BACKGROUND

Premenstrual syndrome ("PMS"), a chronic complaint of a substantial percentage of women between the ages of 12 and 50, manifests in symptoms before and during menses. The symptoms include pain, marked general tension, marked irritability, anxiety, depression, abdominal bloating, swelling of subcutaneous tissues, nausea, fatigue, painful swelling of the breasts, headaches, dizziness, and palpitations. J. T. E. Richardson, "The Menstrual Cycle, Cognition, and Paramenstrual Symptomatology", *Cognition and the Menstrual Cycle*(Springer-Verlag 1992). While virtually all women experience pain at the onset of menstruation, many women also experience some of the listed symptoms several days before the onset of menses. The symptoms vary from one menstrual cycle to another, and vary considerably among individual women. These symptoms are generally conceded to be related to the release of various hormones, including estrogens.

For women who experience severe PMS, there is considerable desire for their pain and suffering to be relieved. Some women find that their cognitive abilities are impaired and hope for ways to improve their cognitive performance during the days when affected by PMS. Id.

Studies have revealed that during PMS, some women develop "food cravings" which adversely affect some aspects of their health. J. J. Rapkin & D. Tonnesses, *A Woman Doctor's Guide to PMS*, (Hyperion, 1994). Generally, these patients are directed to eat regular small meals, decrease their intake of salt, fat, sugar, and caffeine, and increase consumption of whole grains, seed and nuts, vegetables, fruits, and vegetable oils. In addition, vitamins and dietary supplements such as primrose oil are sometimes used by women to alleviate the symptoms of PMS.

Menopause, or "the change of life", occurs when a woman's cycle of ovulation and menses ends. Common symptoms of menopause include hot flashes, excessive sweating, vaginal atrophy, and sleep disturbances. Menopause is a natural consequence of aging caused when a woman's ovaries begin to produce less estrogen. It is widely accepted that the symptoms of menopause result from decreased estrogen in the body. I. Schiff, *Menopause* (Times Books, a division of Random House, 1996). It is often acknowledged that the manifestations of menopause can be alleviated by controlling the diet. For example, it has been observed that women in Japan and China have decreased menopausal severity compared to women in Western countries. In most texts, this is attributed to the consumption of soy products. However, it must be recognized that Asian women also eat substantial amounts of cruciferous vegetables in addition to soy products. The possibility that menopausal symptoms result from changes in estrogen metabolism is seldom mentioned.

Beginning in the 1960's, many symptoms of menopause have been dealt with through estrogen supplementation. B. Kass-Annese, *Management of the Perimenopausal & Postmenopausal Woman* (Lippincott, 1999). More recently, other hormones, such as progesterone, have been employed. Other steroids have been suggested, along with numerous medications, to relieve various symptoms. While many studies have investigated the various hormones which might be taken by various means, little research has been done to investigate the ways in which hormones, particularly estrogens, might be metabolized to alter their physiological effects. 1H-indole-3-methanol (CAS Registry Number [700-06-1]) is a naturally occurring product which is derived from cruciferous vegetables. It is known to exhibit substantial effects in the metabolism of estradiol as reported by many workers, and has been implicated as having potential utility in the treatment of breast cancer. In this regard, one of 1H-indole-3-methanol's pharmacological activities is that of an estradiol 2-hydroxylase inducer. Some of its effects have been summarized in a review by Michnovicz and co-workers. Michnovicz et al. "Changes in Levels of Urinary Estrogen Metabolites After Oral Indole-3-Carbinol Treatment in Humans", *J. Nat'l Cancer Inst.*, 89(10):718–23 (1997). It has also been observed that 1H-indole-3-methanol reacts with itself in stomach acid and under other conditions such as heat, light and even water solutions to form new compounds ("1H-indole-3-methanol compounds"). See, e.g., Michnovicz & Bradlow, "Dietary Cytochrome P-450 Modifiers in the Control of Estrogen Metabolism", *Food Phytochemicals for Cancer Prevention I, Fruits & Vegetables*, pp. 282–293, nn. 89–93, edited by Mou-Tuan et al. ACS Symposium Series 546 (American Chemical Society, Washington, D.C., 1994). Some of these 1H-indole-3-methanol compounds (e.g., diindolylmethane and indolo(3,2-b)carbazole) are reported to bind the same receptors as the 1H-indole-3-methanol. Id.

Although described for the potential treatment of breast cancer and fibromyalgia (see, e.g., U.S. Pat. No. 5,895,787 to Arffmann et al. (Apr. 20, 1999), heretofore, the use of 1H-indole-3-methanol compounds for treating conditions such as PMS and hormone related difficulties associated with menopause is not believed to have been described.

DISCLOSURE OF THE INVENTION

Dietary indoles, particularly, 1H-indole-3-methanol, have been found to greatly relieve the symptoms of premenstrual syndrome (PMS) and menopause. Patients with PMS have reported decreased menstrual cramping, decreased menstrual flow, shorter duration of menses, decreased fatigue, less frequent headaches, improved mood, and decreased bloating resulting from the oral administration of pharmaceutically effective amounts of dietary indoles derived from 1H-indole-3-methanol. Positive results were sometimes seen within one menstrual cycle of using daily doses of 1H-indole-3-methanol compounds. Patients suffering from menopause have reported considerable reductions in hot flashes and sweating profusion and less sleep disturbances resulting from the oral administration of pharmaceutically effective amounts of dietary indoles derived from 1H-indole-3-methanol.

The invention thus includes a method of treating PMS in a patient believed to be suffering therefrom, the method comprising: administering to the patient an 1H-indole-3-methanol compound in a medically acceptable manner in a pharmaceutically effective amount on a daily basis or during a specific portion of the menstrual cycle, such as days 7–21 after menses.

The invention also includes a method of treating menopause in a patient believed to be suffering therefrom, the method comprising: administering to the patient an 1H-indole-3-methanol compound in a medically acceptable manner in a pharmaceutically effective amount on a daily basis.

The invention also includes methods of making a pharmaceutical compositions containing an 1H-indole-3-methanol compound or compounds for use in the treatment of menopause or PMS.

BEST MODE FOR CARRYING OUT THE INVENTION 1H-indole-3-methanol compounds are naturally occurring compounds. These dietary indoles result from the maceration of cruciferous vegetables by the manner briefly described herein. Glucosinolates, a set of compounds containing a glucose component, a sulfur-carbon-nitrogen component, and a variable component, occur in varying ratios in varietals, leaves, stocks, stems, flowers, seeds, and roots of the brassica (or crucifiers) plants. For example, in glucobrassicin, a glucosinolate, the variable component is 3-indolylmethyl. When the cell walls of the plant are destroyed through chopping, grinding, chewing, for example, an enzyme, myrosinase, is released. Myrosinase aids in the hydrolysis of glucobrassicin resulting in the release of 1H-indole-3-methanol, often called indole-3-carbinol. 1H-indole-3-methanol is produced in sufficient quantity that it can be isolated from the juices of many of the cruciferous vegetables such as, for example, cabbage, Brussels sprouts, or broccoli. It has also been shown that 1H-indole-3-methanol can be produced from indole by any of a number of chemical transformations.

Whether derived from cruciferous vegetables or prepared by one of a number of controlled chemical transformations, 1H-indole-3-methanol is a very reactive molecule, unless it is kept cool, dry, and isolated from species with which it easily reacts. 1H-indole-3-methanol is especially reactive with hydroxyl groups.

1-indole-3-methanol will react with ascorbic acid to give ascorbigen, so named because it was once thought to be the origin of ascorbic acid (vitamin C) in cruciferous vegetables. Later studies showed that vegetable juice showed a decrease in ascorbic acid upon standing due to the combination of ascorbic acid with 1H-indole-3-methanol. As previously indicated, 1H-indole-3-methanol has been studied extensively in connection with cancer prevention. It is also used as a dietary supplement to aid in the inhibition of laryngeal papillomatosis.

Numerous studies have shown that four other compounds: a carbazole, namely, indolo[2,3,-b(carbazole)]; a "dimer", bis(3-indolyl) methane; a linear "trimer," namely 2-(indol-3-ylmethyl)-3,3'-diindolylmethane; and a cyclic "trimer," namely 5,6,11,12,17,18-hexahydrocyclonona[1,2-b;4,5-b';7,8-b"]triindole also result from the reactions of 1H-indole-3-methanol with itself. These four additional identified products are only a sampling of the products realized by heating 1H-indole-3-methanol.

It has been shown that the same array of products results from subjecting the 1H-indole-3-methanol to stomach acid, or even acidified water. Consequently, numerous workers have concluded that the mixture of dietary indoles (the "1H-indole-3-methanol compounds"), not just 1H-indole-3-methanol, is responsible for the beneficial effects seen in providing animals and humans with dietary indoles. In fact, cell tissue studies have led workers to conclude that 1H-indole-3-methanol may not be beneficial at the cell level, but that some other derivative, such as the "dimer," the "trimers," the carbazole, and/or perhaps other compound(s) in the dietary indole mixture, is/are the actual entity/entities giving beneficial results.

Whether 1H-indole-3-methanol is derived from the extraction of cruciferous vegetables or is prepared by a chemical reaction in which indole is a starting material, it will result in identical chemical products when ingested by humans. Since 1H-indole-3-methanol is reactive, and positive results are obtained in other applications with the reaction products of 1H-indole-3-methanol, it is believed that not only 1H-indole-3-methanol, but its reaction products, will be effective in mitigating the symptoms of PMS and menopause. This family of indole-containing compounds, including 1H-indole-3-methanol and products derived from the reaction of 1H-indole-3-methanol with itself, are called dietary indoles. The reactive nature of 1H-indole-3-methanol is an important consideration in this invention.

Preferably, the 1H-indole-3-methanol compound used to practice the invention is selected from the group consisting of 1H-indole-3-methanol; ascorbigen; (3-indolyl) methane; indolo[3,2-b(carbazole)]; 2-(indol-3-ylmethyl)-3,3'-diindolylmethane; 5,6,11,12,17,18-hexahydrocyclonona[1,2-b;4,5-b';7,8-b"]triindole; 1H-indol-3-yl methoxy methane; ethoxy 1H-indol-3-yl ethoxy methane; other ethers of 1H-indole-3-methanol, and mixtures of any thereof. Also included within the scope hereof are pharmaceutically acceptable esters of the 1H-indole-3-methanol compounds. Once the 1H-indole-3-methanol compound or compounds has/have been chosen, methods and compositions for making dosage units containing the compounds are well-known to those of skill in the art. For instance, conventional techniques for making tablets, capsules, and pills containing active ingredients are described in the standard reference, Chase et al., *Remington's Pharmaceutical Sciences*, (16$^{th}$ ed., Mack Publishing Co., Easton, Pa., USA, 1980) ("*Remington's*") at pages 1553 through 1584. Conventional techniques for making powders, and their composition, are described at pages 1535 through 1552 of *Remington's*. Conventional techniques for coating pharmaceutical dosage forms are described at pages 1585 to 1593 of *Remington's*.

For making dosage units, e.g., tablets or capsules, the use of conventional additives, e.g., fillers, colorants, binders, and the like is contemplated. In general, any pharmaceutically acceptable additive which does not interfere with the function of the active compound can be used in the compositions.

Suitable carriers with which the compositions can be administered include lactose, starch, cellulose derivatives and the like used in suitable amounts. Mixtures of carriers can also be used.

A process of manufacturing a composition for oral administration of the invention includes mixing predetermined quantities of the active ingredient with predetermined quantities of excipients and converting the mixture into dosage units containing, for example, 5 to 1000 milligrams ("mg"), preferably 25 to 400 mg, of active ingredient.

Converting the mixture into dosage units generally involves molding the mixture into a tablet, filling a capsule with a dry mixture, or filling a capsule with a wet mixture.

Once made, the dosage units may be administered daily or during a specific portion of the menstrual cycle, for example 7–21 days after menses, to achieve the desired dosage.

Although generally less desirable from a patient acceptability view point, the active ingredient may alternatively be parenterally administered in dosages equivalent to the oral dosages described herein (taking into consideration effects such as bioavailability), such as by injection or transdermal delivery.

The invention is further explained by the following illustrative examples.

EXAMPLES

Example I

Relatively pure 1H-indole-3-methanol (I3C™ from Designed Nutritional Products, Orem, Utah, U.S.) in a water solution was prepared for HPLC analysis. One sample was diluted with water and the other was diluted with methanol. By the time the methanol solution of 1H-indole-3-methanol could be injected into the HPLC, the reaction with methanol had taken place to form 1H-indol-3-yl methoxy methane, the methyl ether of 1H-indole-3-methanol and two peaks of about the same magnitude were observed. The water solution of 1H-indole-3-methanol showed only one peak.

Example II

In the course of manufacturing and formulating dietary supplements containing 1H-indole-3-methanol, it was observed that the carbinol in the three position is extremely reactive. In the presence of sunlight, the compound will change color in just a few hours.

In the course of heating at 60° C., 99% of the present 1H-indole-3-methanol will disappear from HPLC chromatograms, being replaced by as many as 40 or 50 different derived compounds, virtually all of them identified as containing an indole component. More detailed studies have shown that one of the first compounds to appear in a sample of 1H-indole-3-methanol undergoing heat treatment is (3-indole-methanol, a "dimer" of 1H-indole-3-methanol.

Example III

Capsules containing 100 to 300 mg of 1H-indole-3-methanol (I3C™ from Designed Nutritional Products, Orem, Utah, U.S.) were made by placing that amount of 1H-indole-3-methanol into gelatin capsules.

Example IV

Capsules containing 100 to 300 mg of bis(3-indolyl) methane were made by placing that amount of compound into gelatin capsules.

Example V

Capsules containing 100 to 300 mg of 1H-indol-3-yl methoxy methane were made by placing that amount of compound into gelatin capsules.

Example VI

Capsules containing 100 to 300 mg of ascorbigen are made by placing that amount of compound into gelatin capsules.

Example VII

Capsules containing 200 mg of 1H-indole-3-methanol (I3C™ from Designed Nutritional Products, Orem, Utah, U.S.) were made by placing that amount of 1H-indole-3-methanol into gelatin capsules.

Example VIII

Subject A, age 13, commonly suffered from fatigue, moodiness, and bluish circles beneath her eyes prior to menstruation. During menses, which typically lasted for 7–10 days, she experienced menstrual cramping which required ibuprofen for relief. Subject A had taken I3C™ for three menstrual cycles. Since taking I3C™, the above symptoms were alleviated and her menses lasted approximately 4 days.

Example IX

Subject B, age 15½, had taken I3C™ for one menstrual cycle. Her PMS symptoms prior to taking I3C™ included extreme fatigue, frequent migraine headaches, bloating, moodiness, and severe menstrual cramps. She started taking I3C™ with no knowledge of its effects or benefits. Within one menstrual cycle, she experienced only mild fatigue and her remaining symptoms were alleviated.

Example X

Subject C, age 41, had been diagnosed and treated for endometriosis. Her PMS symptoms included fatigue, heavy blood flow (menorrhagia), severe menstrual cramps, and menses of approximately 10 days. Subject C had taken I3C™ for six cycles. Since taking I3C™, Subject C's fatigue ceased, her menstrual blood flow decreased substantially, the severity of her menstrual cramps decreased, and her menses shortened to approximately 5 days. Subject C stopped taking I3C™ for one menstrual cycle and her previous PMS symptoms returned. When subject C started taking I3C™ again, her symptoms were alleviated.

Example XI

Subject D, had taken I3C™ for ½ months and noticed a rapid change in her PMS symptoms. She noticed less bloating and reduced headaches.

Example XII

Subject E, age 41, had a partial hysterectomy where her uterus, but not her ovaries, was removed. After the hysterectomy, Subject E had menopausal symptoms including hot flashes, occasional sweating profusion, grogginess after a full night's sleep, and almost continuous irritable bowel syndrome. Subject E started taking four 100 mg capsules of I3C™ per day, two capsules in the morning and two capsules in the late afternoon. She had taken I3C™ for one month and noticed bowel regularity, less sleep disturbances, and a steady energy level throughout the day. Her hot flashes and excessive sweating disappeared after taking a few doses of I3C™.

Although the invention has been described with regard to certain preferred embodiments and examples, the scope of the invention is to be defined by the appended claims.

What is claimed is:

1. A method of alleviating symptoms of a hormone-related difficulty in a subject suffering therefrom, said hormone-related difficulty selected from the group consisting of premenstrual syndrome and menopause, said method comprising: administering to the subject an 1H-indole-3-methanol compound in a medically acceptable manner in a pharmaceutically effective amount to alleviate symptoms of the hormone-related difficulty.

2. The method according to claim 1 wherein the 1H-indole-3-methanol compound is selected from the group consisting of 1H-indole-3-methanol; ascorbigen; bis (3-indolyl) methane; indolo[3,2-b(carbazole)]; 2-(indol-3-ylmethyl)-3,3'-diindolylmethane; 5,6,11,12,17,18-hexahydrocyclonona[1,2-b;4,5-b';7,8-b"]triindole;

1H-indol-3-yl methoxy methane; ethers of 1H-indole-3-methanol; and mixtures of any thereof.

3. The method according to claim 2 wherein the 1H-indole-3-methanol compound is 1H-indole-3-methanol administered to the subject in an amount of from about 5 milligrams to about one gram orally each day.

4. The method according to claim 1 wherein the 1H-indole-3-methanol compound is administered in a single daily dose.

5. The method according to claim 1 wherein the 1H-indole-3-methanol compound is administered during a specific portion of the menstrual cycle.

6. The method according to claim 1 wherein the 1H-indole-3-methanol compound comprises bis (3-indolyl) methane.

7. The method according to claim 1 wherein the 1H-indole-3-methanol compound comprises indolo[3,2-b(carbazole)].

8. The method according to claim 1 wherein the 1H-indole-3-methanol compound comprises 2-(indol-3-ylmethyl)-3,3'-diindolylmethane.

9. The method according to claim 1 wherein the 1H-indole-3-methanol compound comprises 5,6,11,12,17,18-hexahydrocyclonona[1,2-b;4,5-b';7,8-b"]triindole.

10. The method according to claim 1 wherein the 1H-indole-3-methanol compound comprises ascorbigen.

11. The method according to claim 1 wherein the 1H-indole-3-methanol compound comprises 1H-indol-3-yl methoxy methane.

12. The method according to claim 1 wherein the 1H-indole-3-methanol compound comprises an ether of 1H-indole-3-methanol selected from the group consisting of ethoxy 1H-indol-3-yl ethoxy methane, the ethyl ether of 1H-indole-3-methanol and mixtures of any thereof.

13. The method according to claim 1 wherein the 1H-indole-3-methanol compound comprises a mixture of dietary indoles, said dietary indoles selected from the group consisting of 1H-indole-3-methanol; bis (3-indolyl) methane; indolo[3,2-b(carbazole)]; 2-(indol-3-ylmethyl)-3,3'-diindolylmethane; 5,6,11,12,17,18-hexahydrocyclonona[1,2-b;4,5-b';7,8-b"]triindole; ethers of 1H-indole-3-methanol; and ascorbigen.

14. A method of alleviating the symptoms of premenstrual syndrome or menopause in a subject suffering therefrom, said method comprising:

administering to the subject an estradiol 2-hydroxylase inducing compound in a medically acceptable manner in a pharmaceutically effective amount to alleviate the symptoms.

15. The method according to claim 14 wherein the estradiol 2-hydroxylase inducing compound is 1H-indole-3-methanol.

16. The method according to claim 15 wherein the 1H-indole-3methanol is administered orally in an amount of from about 25 to about 400 milligrams per day.

17. The method according to claim 16 wherein the 1H-indole-3methanol is administered orally in an amount of from about 100 to about 200 milligrams per day.

18. The method according to claim 5 wherein the specific portion is for days 7–21 after menses.

19. A method of palliating the symptoms of premenstrual syndrome or menopause in an individual experiencing the symptoms thereof, the method comprising administering to the individual an estradiol 2-hydroxylase inducing compound in a medically acceptable manner in a pharmaceutically effective amount on a therapeutically effective schedule to alleviate the symptoms.

20. The method according to claim 19 wherein the estradiol 2-hydroxylase inducing compound comprises an 1H-indole-3-methanol compound.

* * * * *